(12) United States Patent
Alberti et al.

(10) Patent No.: US 7,521,141 B2
(45) Date of Patent: Apr. 21, 2009

(54) INNOVATIVE METHOD FOR THE PREPARATION OF PROTON CONDUCTING NANOPOLYMERIC MEMBRANES FOR USE IN FUEL CELLS OR IN CATALYTIC MEMBRANE REACTORS

(75) Inventors: Giulio Alberti, Perugia (IT); Mario Casciola, Perugia (IT); Monica Pica, Gualda Tadino (IT)

(73) Assignee: FuMa-Tech Gesellschaft fur funktionelle Membranen und Anlagentechnologie mbH, St. Ingbert (DE)

( * ) Notice: Subject to any disclaimer, the term of this patent is extended or adjusted under 35 U.S.C. 154(b) by 140 days.

(21) Appl. No.: 10/508,748

(22) PCT Filed: Mar. 20, 2003

(86) PCT No.: PCT/EP03/02904

§ 371 (c)(1),
(2), (4) Date: Feb. 7, 2005

(87) PCT Pub. No.: WO03/081691

PCT Pub. Date: Oct. 2, 2003

(65) Prior Publication Data

US 2005/0164092 A1    Jul. 28, 2005

(30) Foreign Application Priority Data

Mar. 22, 2002 (IT) .................. PG 2002 A 0015

(51) Int. Cl.
*H01M 8/10* (2006.01)
*H01M 10/40* (2006.01)
*C08J 5/22* (2006.01)
*C01M 143/02* (2006.01)

(52) U.S. Cl. ............................ 429/33; 429/306; 429/30; 429/40; 429/41; 429/46; 521/27; 508/234

(58) Field of Classification Search ................... 429/33, 429/30, 40, 41, 46, 306; 502/208; 427/115; 521/27; 505/234
See application file for complete search history.

(56) References Cited

U.S. PATENT DOCUMENTS 5,892,080 A * 4/1999 Alberti et al. ............... 556/19
5,919,583 A * 7/1999 Grot et al. .................. 429/33
7,108,935 B2 * 9/2006 Bauer et al. ................ 429/33

FOREIGN PATENT DOCUMENTS

| FR | 2 753 971 A1 | 4/1998 |
|---|---|---|
| IT | MI 002443 | 11/2000 |
| IT | PG 2002 A 0013 | 3/2002 |
| WO | 03/077340 A2 | 9/2003 |
| WO | WO 03077340 A2 * | 9/2003 |

OTHER PUBLICATIONS

Alberti, G., et al., "Layered metal$^{IV}$ phosphonates, a large class of inorgano-organic proton conductors" Solid State Ionics, 97 pp. 177-186 (1997).
Alberti, G. and Bein, T., vol. eds. "Layered Metal Phosphonates and covalently Pillared Diphonsphonates" Supramolecular Chemistry, editor Jean-Marie Lehn, Pergamon, vol. 7, chpt. 5, pp. 151-187 (1996).
Clearfield, A., "Metal Phosphonate Chemistry", Progress in Inorganic Chemistry, editor, Karlin, K.D., vol. 47, pp. 371-509 (1998).
Alberti, G., et al., "Inorgano-organic proton conducting membranes for fuel cells and sensors at medium temperatures", Journal of Membrane Science, vol. 172, pp. 233-239, (2000).
XP-000359485: Alberti, G., et al., "Protonic conductivity of layered zirconium phosphonates containing -SO$_3$H groups. I. Preparation and characterization of a mixed zirconium phosphonate of composition Zr(O$_3$PR)$_{0.73}$(O$_3$PR')$_{1.27}$·$n$H$_2$O, with R=-C$_6$H$_4$-SO$_3$H", Solid State Ionics, vol. 50, pp. 315-322, (1992).
Costamagna, P., et al., "Nafion® 115/zirconium phosphate composite membranes for operation of PEMFCs above 100° C.", Electrochimica Acta, vol. 47, pp. 1023-1033, (2002).
XP-002325215: Rosenthal, G.L., et al., "Synthesis and Structural Analysis of Pure and Mixed Zirconium Phosphonates, Zr(O$_3$PR)×(O$_3$PR')$_{2-x}$", Journal of Solid State Chemistry, vol. 107, pp. 497-502, (1993).
Stein, E.W., et al., "Conductivity of group IV metal sulfophosphonates and a new class of interstratified metal amine-sulfophosphonates", Solid State Ionics, vol. 83, pp. 113-124, (1996).

* cited by examiner

Primary Examiner—Randy Gulakowski
Assistant Examiner—Michael M Bernshteyn
(74) Attorney, Agent, or Firm—The Nath Law Group

(57) ABSTRACT

The invention is based on the preparation of an organic solution of preferably phosphonic acids and tetravalent metals salts, preferably of Zr, Ti, Sn and Ce, in organic solvents, which behaves as a solution of layered tetravalent metals salts, preferably phosphate-phosphonates, which are completely insoluble in the known solvents. This peculiarity allows an easy insertion of particles of the above compounds in the pores of porous membranes, in the matrices of those polymers, which are soluble in the same organic solvents, as well as in the membrane/electrode interfaces of fuel cells. The use of tetravalent metals salts, preferably zirconium phosphate-phosphonates, possessing high proton conductivity (in some cases higher than $10^{-1}$ S cm$^{-1}$) allows the preparation of impregnated porous membranes and of nano-polymeric membranes combining good mechanical properties, and/or reduced permeability to gaseous species, with good proton conductivity. These membranes can therefore be employed in fuel cells even at temperatures higher than 80° C. These membranes also possess a high catalytic activity and can therefore be employed in catalytic membrane reactors.

32 Claims, 1 Drawing Sheet

INNOVATIVE METHOD FOR THE
PREPARATION OF PROTON CONDUCTING
NANOPOLYMERIC MEMBRANES FOR USE
IN FUEL CELLS OR IN CATALYTIC
MEMBRANE REACTORS

BACKGROUND OF THE INVENTION

1. Field of the Invention

The interest for proton conducting polymeric membranes has considerably grown in recent years for their possible use in fuel cells of the PEM FC type (Polymeric Electrolyte Membrane Fuel Cells) that, as well known, are presently the most suitable power supplies for electrical cars or for electrical portable devices such as computers, cellular telephones, telecameras etc. Owing to their strong acid and sometime super acid properties, these proton conducting membranes can also find applications in membrane catalytic reactors, especially for acid, catalysed processes.

Nafion membranes, owing to their excellent chemical stability and high proton conductivity, are presently the most suitable membranes for PEM FC using pure hydrogen as fuel. However, Nafion membranes are very expensive, loss efficiency at temperature higher than 80-90$20$ C. and besides are permeable to methanol.

2. Description of Related Art

This leads to an increase of the already high costs of PEM FC, complicate the cooling of the stacks and does not allow their use in PEM FCs using methanol as fuel. On the other hand, the well-known contamination of the air, provoked, especially in large towns, by the intense vehicular traffic, makes the demand of less pollutant innovative cars more and more urgent. Among the different possible solutions offered by today's technology, presently the preference seems to be oriented towards electrical vehicles fed by PEM FCs. Thus, in the most industrialized countries, attempts are in progress to prepare new proton conducting membranes less expensive and exhibiting better characteristics than Nafion as far as a higher working temperature and a lower permeability to methanol are concerned. All this, in the hope that more economical and more efficient PEM FC may be obtained with these membranes.

Two main research lines are presently followed: a) development of new ionomeric membranes with the above-mentioned characteristics; b) development of membranes prepared with ionomers of the state of art but with improved characteristics.

Concerning the latter point, the improvement of the characteristics of an ionomer can be obtained by taking advantage of the present knowledge on polymeric nano-composites. A polymeric nano-composite (or nano-polymer) is a polymer, which contains an appreciable amount of inorganic nano-particles dispersed as uniformly as possible within its polymeric matrix. Due to the high specific surface of the nano-particles, their interfacial interaction with the polymer matrix may become very strong and may therefore have a deep influence on the properties of the polymer itself. The stronger the interfacial interaction, the greater the influence of the nano-particles on the polymer characteristics. In this respect, the high specific surface of lamellar nano-particles seems to be very convenient. The recent industrial success on polymeric nano-composites containing organophilic clays has clearly demonstrated that the presence of the dispersed lamellar nano-particles, obtained by exfoliation of clays, may indeed modify to a great extent some important properties of the polymers such as inflammability, permeability to neutral or ionic species, mechanical resistance and thermal stability.

The strategy of dispersing fine powders of inorganic compounds such as silica and zirconium phosphate in ionomers of the state of art has been seldom used but it is not new. For example, in the U.S. Pat. No. 5,523,181 it is claimed that silica gel particles dispersed in ionomers favours the maintenance of the water balance, thus allowing the fuel cell to work with reduced humidity in the flux of gaseous reagents. In the Italian patent IT MI 002443 (14 Nov. 2000) has been reported that the presence of silica gel nano-particles or zirconium phosphonate particles in the electrode/membrane interface regions can appreciably improve the performance of hydrogen PEM FC at temperatures >80° C. In the international patent WO 96/29752 of DU PONT DE NEMOURS AND COMPANY (Us/Us) it is claimed that lamellar zirconium acid phosphate too may modify some properties of Nafion, improving for example the mechanical properties or reducing its permeability to methanol. However, it must be pointed out that the addition of non-conducting particles, such as silica, or of particles with low proton conductivity, such as zirconium phosphate, must be limited (usually less than 10 wt %) because the addition of larger amounts could reduce the proton conductivity of the ionomers thus lowering the electrical performance of the fuel cell. Moreover, it must be pointed out that the influence of the dimension and orientation of the particles on the above properties was not well understood and therefore not reported in said international patent. Furthermore, since zirconium phosphate is completely insoluble in known solvents, the insertion has been performed by "in situ precipitation". This method does not give any guarantee either concerning the dimensions and exfoliation degree of the formed precipitates or the orientation of the particles.

BRIEF SUMMARY OF THE INVENTION

The present inventive subject matter is related to organic solutions containing metal(IV) salts and oxoacids of phosphorus from which, after evaporation of the solvent, insoluble compounds of general composition $M(IV)$ $(O_3P\text{-}G)_{2-n}$ $(O_3P\text{—}R^1\text{—}X)_n$ can be obtained, where M(IV) is a tetravalent metal, -G is a generic inorganic or organic group, —$R^1$— is an organic group, —X is an acid group and n is a coefficient ranging from 0 to 1.5.

The tetravalent metal salt of these organic solutions can be an anion and is preferably chosen among carboxylates, chlorides and alkoxides. Further, the tetravalent metal salt is preferably chosen between Zr, Ti, Sn and Ce or their mixture. Further still, the tetravalent salt is preferably the zirconyl propionate or chloride.

The group -G of the organic solutions is preferably chosen among the acid groups —OH; —$R^2$—$SO_3H$ and —$R^2$—$PO_3H_2$, where —$R^2$— is an organic group with preferably linear chain such as —$(CH_2)_m$— and —$(CF_2)_m$—.

The group —$R^1$— of the organic solutions is an arylene group chosen preferably among —$C_6H_4$—; —$C_6H_4$—$CH_2$— and —$C_6H_4$—$CF_2$—.

The acid group —X of the organic solutions is chosen between —$SO_3H$, —$PO_3H_2$ and —COOH.

The solvent may be an inorganic solvent and is chosen among the protonable solvents, especially N,N-dimethylformamide, N-methyl-2-pyrrolidone, dioxane, dimethylsulfoxide, acetamide, acetonitrile, various alkanols and/or their mixtures, commonly used for dissolving the proton conducting ionomers of the state of art.

A further embodiment of the current inventive subject matter is the use of these organic solutions for the insertion of nano-particles of tetravalent metal salts, preferably phosphate-phosphonates, within the pores of polymeric or inorganic porous membranes.

Likewise, methods for the filling of porous membranes with tetravalent metal salts are also contemplated, especially phosphate-phosphonates, based on the following steps: a) preparation of the organic solution described herein, at the same time, may also contain a polymer and/or an ionomer of the state of the art; b) impregnation of the porous membrane with such a solution; c) elimination of the solvent; d) repetition of the steps b and c until the wished percentage of pore filling is obtained.

Even a further embodiment of the current inventive subject matter are proton conducting composite membranes made of polymeric or inorganic porous membranes with pores filled with tetravalent metal salts, especially phosphate-phosphonates, or mixtures of said compounds with a proton conducting ionomer and especially prepared by using the organic solutions described herein.

Likewise, such proton conducting composite membranes wherein the polymeric porous membrane is preferably chosen between those made of chemically and/or thermally stable polymers, especially polytetrafluoroethylene (PTFE) polyvinylidene fluoride (PVDF), polyesters, polyethersulfones and fluoroelastomeres are also contemplated. The proton conducting composite membranes described herein wherein the pore dimensions of the porous membranes are preferably in the range 0.02-20 μm, especially 0.1-10 μm, preferably 0.4-2 μm and the porosity >10%, especially >50%, preferably 65-90% are also provided for.

Even further still, proton conducting composite membranes as described herein wherein the tetravalent metal salts, preferably phosphate-phosphonates, for the filling of pores are chosen between $Zr(O_3P—CH_2—PO_3H_2)_2$ and compounds of the series $Zr(O_3P—OH)_{2-n}(O_3P—C_6H_4—SO_3H)_n$, and $Zr(O_3P—C_6H_4—SO_3H—)_{2-n}(O_3P—CH_2—PO_3H_2)_n$, with n in the range 0.1-1.5 are contemplated. Also, composite membranes made up of a porous ceramic membrane partially filled with a tetravalent metal salt, preferably phosphate-phosphonate, as described herein and exhibiting catalytic activity are also contemplated. Specifically, composite membranes made up of porous ceramic membranes partially filled with tetravalent metal salts, preferably phosphate-phosphonate, are chosen between $Zr(O_3P—CH_2—PO_3H_2)_2$ and compounds of the series $Zr(O_3P—OH)_{2-n}(O_3P—C_6H_4—SO_3H)_n$, and $Zr(O_3P—C_6H_4—SO_3H—)_{2-n}(O_3P—CH_2—PO_3H_2)_n$, with n in the range 0.1-1.5 with catalytic activity are also contemplated.

The use of the organic solutions as described herein for the preparation of nano-polymers constituted by nano-particles of tetravalent metal salts as described herein, preferably phosphate-phosphonates, dispersed in the matrix of organic or inorganic polymers soluble in the same solvents is contemplated. Likewise, the use of the organic solutions as described herein for the preparation of the nano-polymers described herein wherein the organic polymeric matrix is that of a proton conducting ionomer is also provided for.

Also provided for are methods for the preparation of nano-polymers and nano-ionomers as described herein based on: a) preparation of an organic solution as described herein and at the same time containing a polymer and/or an ionomer of the state of the art; b) elimination of the solvent. These methods described herein also provide for the preparation of nano-polymers and nano-ionomers as described herein wherein the elimination of the solvent is preferably performed by evaporation or with a non-solvent of the polymer or ionomer.

Also contemplated are nano-polymers constituted by nano-particles of tetravalent metal salts, preferably phosphate-phosphonates, dispersed in the matrix of organic or inorganic polymers. These nano-polymers as described herein wherein the polymeric matrix is that of a synthetic ionomer of the state of the art preferably chosen among perfluorosulphonic polymers, sulfonated polyetherketones (sPEK), sulfonated polyethersulfones and sulfonated polyvinylidenfluoride (sPVDF) are also provided for, as are the nano-polymers as described herein wherein the nano-particles of tetravalent metal salts, preferably phosphate-phosphonates, dispersed in the polymeric matrix are chosen among those exhibiting proton conductivity $>10^{-2}$ S cm$^{-1}$ at 70° C. and 95% relative humidity. Further still, these nano-polymers as described herein wherein the nano-particles of tetravalent metal salts, preferably phosphate-phosphonates, are chosen between $Zr(O_3P—CH_2—PO_3H_2)_2$ and compounds of the series $Zr(O_3P—OH)_{2-n}(O_3P—C_6H_4—SO_3H)_n$, and $Zr(O_3P—C_6H_4—SO_3H—)_{2-n}(O_3P—CH_2—PO_3H_2)_n$, with n in the range 0.1-1.5 with catalytic activity are also contemplate The use of the organic solutions as described herein for an easy insertion of a large variety of lamellar nano-particles of tetravalent metal salts, preferably phosphate-phosphonates, in the membrane/electrode interfaces of PEM FCs is also provided for. Also, the use of the organic solutions as described herein, with the addition of ionomers and/or other proton conducting compounds soluble in the same solvents, for an easy insertion of a large variety of lamellar nano-particles of tetravalent metal salts, preferably phosphate-phosphonates, in mixture with other proton conducting compounds in the membrane/electrode interfaces of PEM FCs is also contemplated.

Further still, the use of proton conducting membranes constituted by inorganic or polymeric porous membranes with pores filled with tetravalent metal salts, preferably phosphate-phosphonates, as described herein and of membranes constituted by nano-polymers as described herein, in electrochemical devices is also contemplated. The use of proton conducting membranes as described herein in electrochemical devices specifically planned for generating electrical energy from the oxidation of a fuel is also provided for, as is the use of proton conducting membranes of as described herein in fuel cells specifically planned for electrical vehicles and/or for portable electrical devices. Also provided for are the uses of composite membranes as described herein for improving the global performance of ionomeric membranes of the state of the art in hydrogen, indirect methanol and direct methanol fuel cells and the use of the membranes described herein in catalytic membrane reactors.

DETAILED DESCRIPTION

Figure 1:
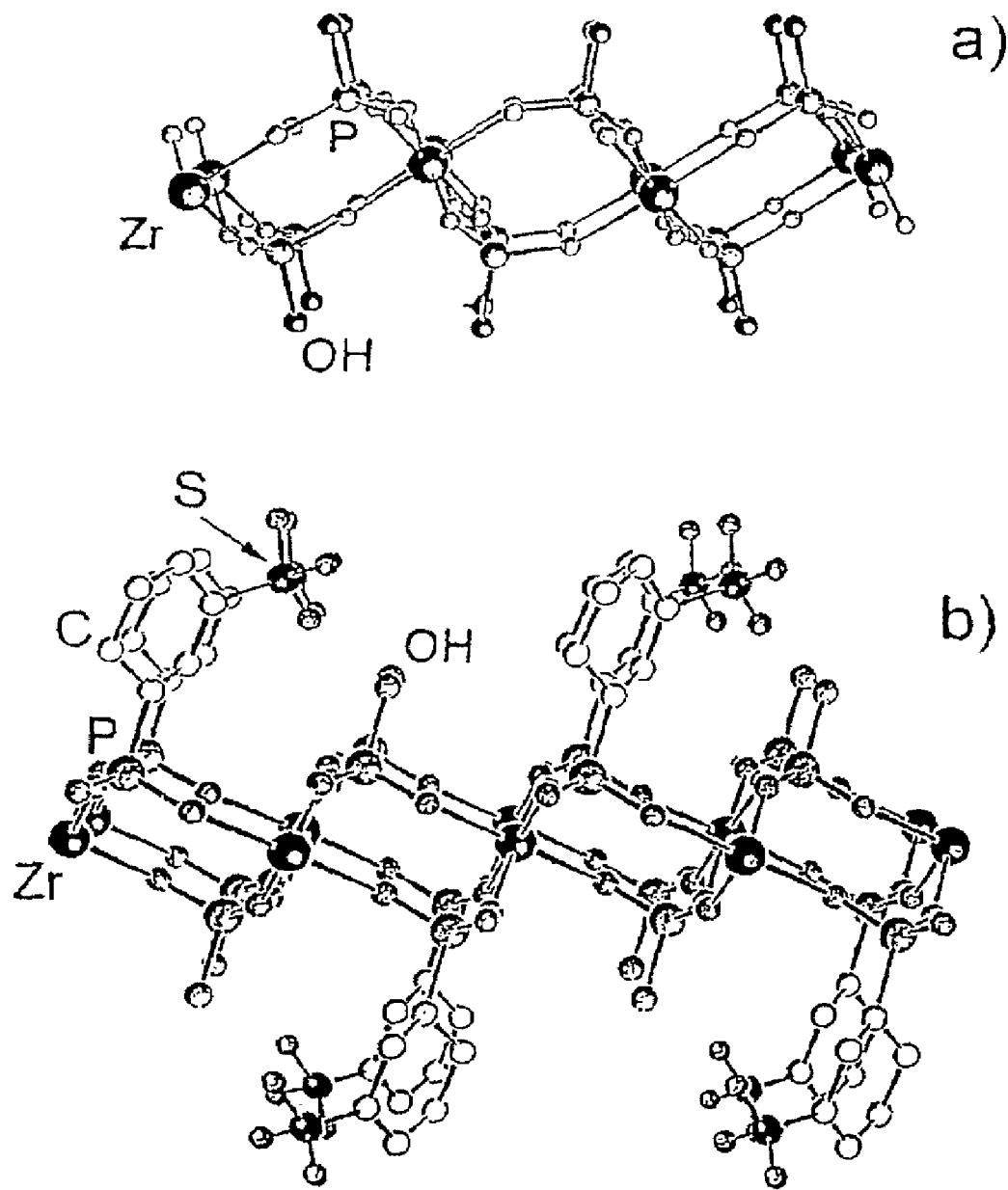
FIG. 1a) The typical layered α-structure of organic derivatives of the corresponding layered metal(IV) phosphates FIG. 1b) Shows a schematic view of a single lamella of the compound $Zr(O_3P—OH)(O_3P—C_6H_4—SO_3H)$ where G=—OH; —R$^1$—=—C$_6$H$_4$—; —X=—SO$_3$H).

In order to prepare proton conducting composite membranes exhibiting better properties than pure membranes of the state of art, it was recognized the need of a more appropriate method for the insertion of the insoluble lamellar particles in the ionomeric matrix and of using particles with proton conductivity much higher than zirconium phosphate and preferably higher than or comparable to that of the ionomer in which the particles have to be dispersed.

In a previous Italian patent (IT PG 2002A 0013 del 13 Mar. 2002), it was claimed the use of exfoliated metal(IV) phosphate-sulfoarylenphosphonates with high proton conductivity (e.g., >$10^{-2}$ S $cm^{-1}$) for improving the properties of polymeric proton-conducting membranes less expensive than Nafion such as polyetheretherketone membranes.

The present invention is also related to the preparation of polymeric nano-composites containing metal (IV) salts, preferably phosphate-phosphonates, of tetravalent metals dispersed in a polymeric matrix. The nano-polymers are not obtained as reported in said Italian patent but a completely different strategy is followed. This strategy, as it will be reported in detail later, does not only allow the use of a very large number of phosphate-phosphonates of tetravalent metals and makes the process of nano-composite preparation much easier and more economical, but also allows a further extension of the present invention to other applications of interest as, for example, the filling of the pores of polymeric or ceramic membranes with nano-particles exhibiting very high proton conductivity and catalytic activity or the insertion of inorganic particles in the electrode/membrane interfaces.

It is well known that metal(IV) phosphate-phosphonates are members of a very large family of lamellar compounds. They can be seen as organic derivatives of the corresponding layered metal(IV) phosphates among which the most investigated compound is the zirconium phosphate, Zr($O_3$P—OH)$_2$, exhibiting the typical layered α-structure, schematically illustrated in FIG. 1a. The compositions of possible metal(IV) phosphate-phosphonates can be very different from each other since the phosphonate groups can be chosen among a large variety of species and even their mixtures in different ratios can be used. Thus, for sake of brevity, when a more precise definition of the composition is not necessary, the zirconium phosphate-phosphonates will be here simply indicated by the general formula M(IV) ($O_3$P-G)$_{2-x}$($O_3$P—$R^1$X)$_n$ where M(IV)=Zr, Ti, Sn or Ce; G is an inorganic (e.g., —OH) or organic (e.g., —$CH_2$OH) or an inorganic-organic group (e.g., —$CH_2$—$SO_3$H; —$CF_2$—$PO_3H_2$); $R^1$ is an arylene group (e.g., phenylen); X is an acid group chosen between —$SO_3$H, —$PO_3H_2$ and —COOH; n is a coefficient which can vary between 0 and about 1.5. In this formulation, the $O_3$P— (i.e. written with the three oxygens to the left of phosphorus) indicates that each phosphorus is bonded to three different zirconium atoms through three oxygens, as in the lamellar structure of α-zirconium phosphate. As an examples a schematic view of a single lamella of the compound Zr($O_3$P—OH)($O_3$P—$C_6H_4$—$SO_3$H) (i.e., where G=—OH; —$R^1$=—$C_6H_4$—; —X=—$SO_3$H) is shown in part (b) of FIG. 1.

The metal(IV) phosphate-phosphonates are very insoluble in water and in organic solvents and exhibit a very high protonic conductivity (in some cases >$10^{-1}$ S $cm^{-1}$) if they possess very acidic groups. More detailed information on the proton conductivity of these lamellar compounds can be found, for example, in G. Alberti, M. Casciola Solid State Ionics 97, 177 (1997), while information on the chemistry of these compounds can be found in the chapter 5 of volume 7 of the series Comprehensive Supramolecular Chemistry (volume editors G. Alberti and T. Bein; editor of the series Jean-Marie Lehn), Pergamon 1996 and in the review A. Clearfield "Metal phosphonate chemistry" in "Progress in Inorganic Chemistry", volume 47, p. 371-509, John Wiley & Sons, 1998.

In the cited Italian patent it is claimed that lamellar metal (IV) acid phosphates and phosphate-sulfoarylenphosphonates (e.g., Zr($O_3$P—OH)$_{2-x}$($O_3$P—$C_6H_4$—$SO_3$H)$_x$) appreciably exfoliate in water and in some organic solvents, (e.g., DMF and $CH_3$CN and/or their mixtures) which are used for the solubilization of proton conducting ionomers.

The possibility of forming colloidal dispersions of these compounds in the solvents that are able to solubilize the ionomers of the state of the art made it easier to disperse the layered nano-particles of these compounds in the polymeric matrix of the ionomers.

The preparation of the nano-polymers is carried out in four steps: 1) the preparation of the wanted metal(IV) phosphate-sulfoarylenphosphonate; 2) the formation of its dispersion in an organic solvent of the ionomer to be modified; 3) the mixing of this dispersion with a solution of the ionomer; 4) the evaporation of the solvent.

This invention has represented a considerable progress relatively to the international patent WO 96/29752 already cited, where the insertion of the lamellar compound in the polymeric matrix has been performed by "in situ precipitation" and where the chosen compound was the zirconium phosphate which exhibits a modest proton conductivity (this conductivity can vary in a large range, depending on the crystallinity degree, on the particle size, on the temperature and relative humidity, but the maximum values are of the order of $10^{-3}$ S $cm^{-1}$). The new method allowed a better control of the size and orientation of the dispersed lamellar particles; furthermore, the method used for the first time lamellar compounds exhibiting proton conductivity 10-100 times higher than that of zirconium phosphate. This allowed the preparation of nano-ionomers with higher proton conductivity than that of the corresponding ionomers filled with zirconium phosphate.

It was surprisingly found that if the preparation of metal (IV) phosphate-phosphonates is directly carried out in the organic solvents commonly used for dissolving sulfonated ionomers or other polymers (e.g., N,N-dimethylformamide (DMF), N-methyl 2-pyrrolidone (NMP), dioxane, dimethylsulfoxide (DMSO), acetonitrile, alkanols etc, and/or their mixtures) the formation of the metal(IV) phosphate-phosphonates takes place very slowly at temperatures <40° C. so that precipitation or gel formation are not observed even after many days. It was also found by the inventors that the stability of these solutions depends on the temperature, on the composition of the metal(IV) phosphate-phosphonates and on the concentration of the initial solution. For example, if in 0.1 liter of NMP 0.1 mol of phosphoric acid, 0.1 mol of sulfophenylenphosphonic acid and 0.1 mol of zirconium propionate (i.e., reagents corresponding to the stoichiometric formation of a zirconium phosphate-sulfoarylenphosphonate with -G=—OH; —$R^1$=—$C_6H_4$— and x=1) are solubilized at about 20° C., no formation of gels or precipitation takes place. As time passes, a gradual increase of the viscosity of the solution is observed and a gel is finally formed only after 8-10 days. The gelation time considerably decreases at higher temperatures. For example, at 80-90° C. the same solution gives a gel only after some minutes. From these gels, after evaporation of the solvent and elimination of the propionic acid formed in the reaction at 120-140° C., the anhydrous product of composition Zr(HPO$_4$)(PO$_3$—$C_6H_4$—$SO_3$H) is obtained.

Magic angle $^{31}$P solid state NMR showed that the oxoacids of the phosphorus are coordinated to zirconium as in the lamellar structures of α-type (i.e., through three oxygens) while X-ray powder diffraction patterns showed that the first reflection corresponds to the interlayer distance (1.9 nm) of an α-type compound of composition Zr($O_3$P—OH)($O_3$P—$R^1$—$SO_3$H) obtained by precipitation in an aqueous medium. Besides, the proton conductivity is of the same order of magnitude compared to the same compound prepared in an aqueous medium. Although additional experimental evidence is necessary to draw definitive conclusions, it is therefore reasonable to conclude that also the compounds obtained after drying of the said gels have a layered structure of α-type and, in their anhydrous state, they can be formulated as $M(IV)(O_3P-OH)_{2-n}(O_3P-R^1-SO_3H)_n$. However, it must be pointed out that the type of lamellar structure is not significant for the present invention because it is essentially based on the experimental facts that, after solvent elimination from said organic solutions (e.g. by evaporation), it is possible to obtain compounds that, after thermal treatment at 120-140° C., become insoluble in all known solvents and that in some cases exhibit very high proton conductivity.

It was found that the results obtained for zirconium phosphate-sulfoarylenphosphonates can be extended to the whole class of zirconium phosphate-phosphonates.

No specific research to explain the reasons of the delayed precipitation of metal(IV) phosphate-sulfoarylenphosphonates in the above organic solvents has been carried out up to now.

Without wishing the present invention to be bound to any particular theory, it is reasonable to assume that the phosphonic acids may strongly interact with proton acceptor solvents, thus decreasing their acid activity. Therefore, the rate of the global reaction which leads, for example, to the generic $Zr(O_3P-G)_{2-n}(O_3P-R^1-X)_n$ compound (where G, $R^1$, X and n have the same meaning previously reported) could be considerably slowed down, especially at low temperatures. Thus, only soluble intermediate compounds such as small clusters of zirconyl phosphate-phosphonates could be initially formed; then, these clusters grow in size and concentration thus leading to the formation of dense gels. During the drying of such gels (e.g. at temperatures higher than 80° C.) the reaction can be completed with the transformation of these intermediate clusters into the final zirconium phosphate-phosphonate with layered structure. Once formed, these compounds become insoluble in solvents.

In any case, independently of their nature, the above solutions behave, from a practical point of view, as solutions of insoluble metal(IV) phosphate-phosphonates because, after drying, insoluble compounds with the wished composition are obtained.

In other words, these solutions have a behaviour similar to that of some solutions of organic compounds, from which, after polymerisation, insoluble polymers can be obtained. This is of great technological importance because it allows the use of these solutions as true solutions of very insoluble compounds. This peculiarity can be utilized, for example, for filling the pores of porous membranes with the said metal(IV) salts, preferably phosphate-phosphonates. If the membrane is first soaked with the organic solution and then the solvent is eliminated, said insoluble compounds are formed directly inside the pores. In this connection, it must be pointed out that all attempts till now carried out to fill the pores with colloidal dispersions of exfoliated lamellar compounds, both in water and in organic solvent, always showed that only the solvent can enter in the pores while the lamellar particles remain on the membrane surface.

Another objective of the invention is a method for the filling of porous membranes wherein the filling of pores is carried out by (1) closing the bottom of a tube with the membrane, (2) pouring in the tube an amount of the organic solution sufficient to completely cover the inner face of the membrane, (3) sealing the upper part of the tube in order to avoid the evaporation of the organic solvent and (4) allowing solvent evaporation from the external face of the membrane eventually assisted with a gas flow so that the filling of pores takes place starting from that face. The final elimination of the solvent in the membrane is preferably performed by evaporation of the solvent and the reaction of transformation of the residual solid thus obtained into the final tetravalent metal phosphate-phosphonate compound is completed by heating at 120-150° C. for 5-10 hrs.

The peculiarity of the organic solutions of the present invention can also be exploited for another important application because the solvents of these solutions are fortunately the same solvents commonly used for dissolving various polymers, and in particular acid proton conducting ionomers such as Nafion, polyetherketones etc. It is possible to insert lamellar metal(IV) salts, preferably phosphate-phosphonates, nano-particles in the matrix of organic polymers by means of the simple mixing of the two solutions and subsequent solvent evaporation so as to form the wished particles inside the polymeric matrix.

Note that the invention allows the preparation of a large number of different solutions, with the concentrations, and the formation of metal(IV) salts, preferably phosphate-phosphonates, with a great variety compositions and different properties. The present invention can therefore be used for the preparation of a large variety of hybrid polymers and ionomers with the wished properties.

The said organic solutions are very suitable also for the preparations of hybrid membranes either in laboratory scale or with automatic or semi-automatic machinery such as "Erichsen film casting processor". The solutions containing sulfoarylenphosphonic acids assume a particular relevance, due to the high proton conductivity of the compounds containing $-SO_3H$ groups. In this respect, also some solutions containing diphosphonic acids were found of great interest. From these solutions the formation of compounds with general formula $Zr(O_3P-R^2-PO_3H_2)_2$ or $Zr(O_3P-R^2)_{2-n}(O_3P-C_6H_4-PO_3H_2)_n$, where $R^2=-CH_2-$, $-CF_2-$ or $-(CF_2)_n-$ groups, can be obtained when the solvent is eliminated. Mixed compounds such as $Zr(O_3P-R^2-PO_3H_2)_{2-x}(O_3P-C_6H_4-PO_3H_2)_x$ and $Zr(O_3P-R^2-PO_3H_2)_{2-n}(O_3P-C_6H_4-SO_3H)_n$ with n in the range 0-1.5, may be also obtained.

The compound of composition $Zr(O_3P-CH_2-PO_3H_2)_2$, obtained by evaporating the organic solvent, exhibited a very high protonic conductivity (about $4*10^{-2}$ S cm$^{-1}$ at 70° C. and 95% relative humidity). High proton conductivity for compounds that do not contain $-SO_3H$ acid groups is of interest also for the development of protonic conductors stable at temperatures greater than 200° C., where the $-SO_3H$ acid groups cannot be used because of their thermal degradability.

The organic solutions of the present invention can also be used for another important application in the field of PEM FC. These solutions, or their mixtures with proton conducting ionomers such as Nafion or sulfonated polyetherketones (s-PEK), can be sprayed over the electrodes of the fuel cells. In such a way it is possible to insert a large variety of lamellar nano-particles with high proton conductivity in the electrode/membrane interfaces of PEM FCs. This represents a significant improvement of the method described in the Italian patent MI 0022443.

An objective of the present invention is the preparation of organic solutions containing tetravalent metal salts and mixtures of phosphorus oxoacids that, at room or lower temperature, do not give place to gelations or precipitations for a sufficiently long time (at least one hour) and from which, after evaporation of the solvent, it is possible to obtain directly insoluble compounds of composition $M(IV)(O_3P-G)_2$ or of mixed compositions such as $M(IV)(O_3P-G)_{2-n}(O_3P-R^1-$ $SO_3H)_n$ or $M(IV)(O_3P\text{-}G)_{2-n}(O_3P\text{---}R^1\text{---}PO_3H_2)_n$ where G, $R^1$ and n have the same meaning as before defined.

It is a further objective of the present invention to use said solutions for obtaining an easy filling of the pores of porous membranes either of polymeric or ceramic type. The complete filling of the pores with compounds exhibiting high proton conductivity allows the preparation of membranes thin enough and with a good protonic conduction for their use in fuel cells.

The partial filling of the pores with compounds which possess a high catalytic activity allows the preparation of membranes that may be used in membrane catalytic reactors.

It is a further objective of the present invention to use said solutions for obtaining an easy insertion of nano-particles of said compounds within organic or inorganic polymeric structures provided that they are soluble in the same solvents. The use can be extended also to polymers soluble in different solvents from those of the organic solutions object of the present invention, provided that they are mixable with said organic solutions and do not provoke a fast gelation of the solution or the precipitation of the compound to be dispersed in the polymeric matrix.

It is a further objective of the present invention to use said solutions for obtaining an easy insertion of nano-particles of said compounds in proton conducting ionomers with the formation of proton conducting nano-structured ionomers. As reported in the previous cited patent, the insertion of lamellar nano-particles with high proton conductivity allows the preparation of nano-ionomeric membranes, which combine improved mechanical properties (hence less swelling) and/or a decreased permeability to methanol or to hydrogen with high proton conductivity. Another objective of the invention is a method for the preparation of membranes made up by nano-polymers constituted by nano-particles of tetravalent metal phosphate-phosphonates dispersed in the matrix of organic or inorganic polymers based on the following steps: (a) preparation of an organic solution and containing, at the same time, a polymer or an ionomer of the state of the art, (b) use of such an organic solution for preparing a nano-polymer as a membrane by a known technique of the state of the art, (c) elimination of the organic solvent and hydration for preparing a nano-polymeric membrane containing the wished weight percentage of the lamellar compound and exhibiting the required characteristics for a particular application.

In one specification of the above method the organic solution of the step (a) is poured on a plane surface, preferably a glass plate, in order to obtain a flat and thin layer; the solvent is then eliminated by drying for 1 hr. at 80-90° C. and for about 2 hrs at 120-140° C. The resulting membrane is finally detached from the support. For making up the membrane out of the solution of step (a) it can be advantageous to use a semiautomatic film casting processor.

It is a further objective of the present invention to use said solutions for the easy insertion of a large variety of lamellar nano-particles of metal(IV) salts, preferably phosphate-phosphonates, in the electrode/membrane interfaces of PEM FCs, either as pure compounds or in mixture with ionomers such as Nafion and s-PEK.

The invention is based on the preparation of an organic solution of phosphonic acids and salts of tetravalent metals in organic solvents, which behaves as a solution of layered phosphate-phosphonates of the corresponding metals, which are completely insoluble in the known solvents. This peculiarity allows an easy insertion of particles of the above compounds in the pores of porous membranes, in the matrices of those polymers, which are soluble in the same organic solvents, as well as in the membrane/electrode interfaces of fuel cells. The use of zirconium phosphate-phosphonates possessing high proton conductivity (in some cases higher than $10^{-1}$ S cm$^{-1}$) allows the preparation of impregnated porous membranes and of nano-polymeric membranes combining good mechanical properties, and/or reduced permeability to gaseous species, with good proton conductivity. These membranes can therefore be employed in fuel cells even at temperatures higher than 80° C. These membranes also possess a high catalytic activity and can therefore be employed in catalytic membrane reactors.

The following examples have the purpose of facilitating the understanding of the invention, and do not intend to limit in any manner its scope, which is solely defined by the appended claims.

EXAMPLES

Example 1a (This example illustrates the detailed preparation of an NMP solution containing a zirconium salt and oxoacids of phosphorus from which a layered zirconium phosphate-phosphonate of composition $Zr(O_3P\text{---}OH)(O_3P\text{---}C_6H_4\text{---}SO_3H)$ is obtained. Some data on the stability of these solutions, the interlayer distance and the proton conductivity of the obtained solids are also reported).

20.6 g of zirconyl propionate (Magnesium Elektron Limited, England) are dissolved in 53 g of NMP. Taking into account that the composition of this compound was found to be $ZrO_{1.36}(CH_3CH_2COO)_{1.28}$ (MW=206 Dalton), the above amount corresponds to 0.1 mol.

Separately, 0.1 mol of anhydrous sulfophenylenphosphonic acid (23.8 g) and 0.1 mol of anhydrous phosphoric acid (9.8 g) are dissolved in 65 g of NMP. The former solution is slowly added, under stirring at room temperature, to the last solution. A clear solution is obtained. If this solution is maintained at temperature ≦30° C., no precipitation or gel formation is observed for at least a week. When the solution is warmed at temperature ≧80° C., the formation of a compact and transparent gel is observed (it takes usually less than 30 minutes). The solid obtained by evaporation of the solvent at 80° C. does not contain, as shown by $^1$H NMR measurements, appreciable amount of propionates, but the presence of a large amount of NMP is still well evident. When the solvent is then completely eliminated at 130-140° C., a solid of composition $Zr(O_3P\text{---}OH)(O_3P\text{---}C_6H_4\text{---}SO_3H)$ is obtained. The interlayer distance of this compound, determined by X-ray powder diffraction pattern, is 1.9 nm.

The protonic conductivity is $3.2*10^{-2}$ S cm$^{-1}$ at 100° C. and 95% relative humidity.

Example 1b (This example illustrates the detailed preparation of a solution containing a zirconium salt and methandiphosphonic acid in an NMP solution from which, after evaporation, it is possible to obtain a zirconium diphosphonate of composition $Zr(O_3P\text{---}CH_2\text{---}PO_3H_2)_2$. Some data on the stability of the solution and on the proton conductivity of the compound collected after the evaporation of the solvent are also reported).

According to a procedure analogous to that described in Example 1a, 0.1 mol of anhydrous zirconyl propionate are dissolved in 53 g of NMP while 0.2 mol of anhydrous methandiphosphonic acid (35.2 g) are dissolved in 65 g of NMP. The solution of methandiphosphonic acid is then slowly added, at room temperature and under stirring, to the solution of zirconyl propionate. A clear solution is obtained. The behaviour of the obtained solution at temperatures $\leq 30°$ C. and at temperatures $\geq 80°$ C. is very similar to that of the solution described in example 1a. Solvent evaporation at 80° C. leaves a residue which, after heating at 130-140° C., is completely converted into an amorphous solid of composition $Zr(O_3P—CH_2—PO_3H_2)$. The protonic conductivity is $4.0*10^{-2}$ S cm$^{-1}$ at 100° C. and 96% relative humidity.

Example 1c (This example illustrates the preparation of a solution in NMP from which a zirconium methandiphosphonate-sulfophenylenphosphonate of composition $Zr(O_3P—CH_2—PO_3H_2)_{1.5}(O_3P—C_6H_4—SO_3H)_{0.5}$ can be obtained. The stability, the interlayer distance and the proton conductivity of the solid collected after the evaporation of the solvent are also reported).

According to a procedure analogous to that described in Examples 1a and 1b, a clear solution containing 0.15 mol of anhydrous methandiphosphonic acid, 0.05 mol of anhydrous sulfophenylenphosphonic acid (23.8 g) and 0.1 mol of anhydrous zirconyl propionate in 118 g of NMP is prepared.

The behaviour of this solution at temperature $\leq 30°$ C. and at temperature $\geq 80°$ C. is very similar to that of the solution described in example 1a. Solvent evaporation at 80° C. leaves a residue which, after heating at 130-140° C., is completely converted into a solid of composition $Zr(O_3P—CH_2—PO_3H_2)_{1.5}(O_3P—C_6H_4—SO_3H)_{0.5}$ is obtained. The protonic conductivity is $1.0*10^{-1}$ S cm$^{-1}$ at 60° C. and 98% relative humidity.

Example 2a (This example gives a detailed description of the use of the organic solutions reported in examples 1a-1c, or similar, to fill the pores of a porous polymeric membrane with a zirconium phosphonate to obtain a membrane with a good protonic conductivity. Case of a porous polytetrafluoroethylene (PTFE or Teflon) membrane. The protonic conductivities of the membranes filled with some zirconium acid phosphonates are reported).

A clear NMP solution containing an amount of reagents corresponding to 20-30 wt % of the zirconium phosphate-phosphonate chosen for the filling of the porous membrane is prepared according to the procedure described in the examples 1a-1c. A PTFE membrane (Mupor micro porous PM9P, Porex Corporation, GA, USA, pore size 1.0 µm; thickness 0.0051 cm; porosity 30%) is out gassed under vacuum in a desiccator. The membrane, kept under vacuum at room temperature, is then completely covered with the solution for about 10-20 min. The atmospheric pressure is re-established and the membrane is maintained covered by the solution for about 1 hr in order to permit a good infiltration of the solution inside the pores. The membrane is taken out from the solution and the liquid excess on the external faces of the membrane is quickly eliminated (e.g., by contacting alternatively the two membrane faces with a paper filter) while the solvent inside the pores is eliminated by drying at 80° C. for about 1 hr and then at 120-130° C. for about 3 hrs. The entire filling procedure is repeated several times depending on the wished pore filling degree.

Alternatively, especially when a gradient of impregnation is required, the membrane is placed in the bottom of an open tube (made for example of glass or another material insoluble in the used solvent) so as to hermetically seal the low part of the tube. A small volume of the organic solution, but sufficient to completely cover the inner membrane surface, is poured in the tube. To avoid solvent evaporation from the upper part of the tube, this part is well plugged. The solvent is allowed to evaporate slowly only through the external face of the membrane and, if wished, the slow evaporation can be assisted by a tepid airflow. In such a way, the filling of the pores takes place starting from the external side of the membrane. Some proton conductivity values (at 65° C. and 98% relative humidity.) of said porous membrane filled with zirconium phosphate-phosphonates, zirconium diphosphonate-phosphonates and zirconium diphosphonates are reported:

Membrane filled with 54 wt % of $Zr(O_3P—C_6H_4—SO_3H)(O_3P—OH)$:
Proton conductivity: $1.3*10^{-2}$ S cm$^{-1}$.
Membrane filled with 45 wt % of $Zr(O_3P—CH_2—PO_3H_2)_2$ and 10% Nafion 1100:
Proton conductivity: $2.1*10^{-2}$ S cm$^{-1}$.
Membrane filled with 49 wt % of $Zr(O_3P—CH_2—PO_3H_2)_{1.3}(O_3P—C_6H_4—SO_3H)_{0.7}$ and 3% Nafion 1100: Proton conductivity: $3.6*10^{-2}$ S cm$^{-1}$.

Example 2b (This example illustrates the use of the organic solutions reported in the examples 1a-1c or similar, for a partial filling of the pores of a porous inorganic membrane with a super acid zirconium phosphonate in order to prepare a membrane with super acid catalytic properties. Case of a zircon tubular asymmetrical ceramic membrane filled with particles of composition $Zr(O_3P—OH)(O_3P—C_6H_4—SO_3H)$).

A clear NMP solution containing an amount of reagents corresponding to 20-30 wt % of the zirconium phosphate-phosphonate of composition $Zr(O_3P—OH)(O_3P—C_6H_4—SO_3H)$ is prepared according to the procedure described in the example 1a.

A zircon tubular asymmetrical ceramic membrane (TAMI tri-channel, thickness of thin layer 0.14 µm) is out gassed under vacuum in a desiccator. The membrane, kept under vacuum at room temperature, is then completely covered with the solution for about 10 min. Then the same procedure described in example 2a followed. The number of the filling steps is chosen in order to have a partial filling of the pores, preferably in the range 30-70%, with particles of composition $Zr(O_3P—OH)(O_3P—C_6H_4—SO_3H)$.

Example 3a (This example illustrates the use of the organic solutions reported in the examples 1a-1c for preparing a hybrid membrane made of a polymeric matrix filled with a given percentage of the wished nano-particles. Case of the polyvinylidene fluoride (PVDF) filled with 40 wt % of particles having composition $Zr(O_3P—OH)_{0.7}(O_3P—C_6H_4—SO_3H)_{1.3}$. The proton conductivities of membranes made of the pure polymer and of the hybrid polymer, respectively, are reported).

According to a procedure analogous to that described in the examples 1a and 1c, a solution containing 0.07 mol of anhydrous phosphoric acid, 0.13 mol of anhydrous metasulfophenylenphosphonic acid and 0.1 mol of anhydrous zirconium propionate in 118 g of NMP is prepared. Separately, 2.0 g of PVDF are dissolved in 18 g of NMP. Then, 5 g of the former solution are added to the last solution. The resulting solution is stirred for about 1 hr at room temperature and then poured on a glass plate. The solvent is evaporated for about 1 hr at 80-90° C. and then for about 2 hrs at 120-130° C. The membrane is then detached from the glass support by immersion in water, washed with a diluted HCl solution, washed again with deionised water and stored in water at room temperature. The membrane (thickness 0.006 cm) is transparent. The percentage of the compound of composition $Zr(O_3P\text{—}OH)_{0.7}(O_3P\text{—}C_6H_4\text{—}SO_3H)_{1.3}$ in the anhydrous membrane is 40 wt %. The protonic conductivity is $5*10^{-3}$ S cm$^{-1}$ at 100° C. and 95% relative humidity. The protonic conductivity of the pure polymer membrane prepared under similar conditions is negligible ($<10^{-6}$ cm$^{-1}$).

Example 3b (This example illustrates the use of the organic solutions reported in the examples 1a-1b for preparing a hybrid membrane consisting of a polymeric matrix of a proton conducting ionomer of the state of art filled with the wanted percentage of nano-particles. Case of sulfonated polyetheretherketone (s-PEK) filled with 9.5 wt % particles of $Zr(O_3P\text{—}OH)(O_3P\text{—}C_6H_4\text{—}SO_3H)$. The protonic conductivities of membranes made of the pure and hybrid ionomer are reported).

2.0 g of s-PEK 1.4, with ion-exchange capacity $1.4*10^{-3}$ equivalent/g, previously dehydrated at 80° C. overnight are dissolved in 24 g of NMP at 80° C. To this solution 0.85 g of the solution of example 1a are added. The resulting mixture is kept under stirring for 1 hr. With this solution a membrane is prepared according to the procedure described in example 2a.

A transparent membrane (thickness 0.005 cm) is obtained. The weight percentage of the anhydrous zirconium phosphate-phosphonate $Zr(O_3P\text{—}OH)(O_3P\text{—}C_6H_4\text{—}SO_3H)$ in the anhydrous membrane is 9.5%. The protonic conductivity is $6.6*10^{-3}$ S cm$^{-1}$ at 100° C. and 95% relative humidity. The protonic conductivity of a membrane of pure s-PEK 1.4, prepared under similar conditions, is $5.1*10^{-3}$ S cm$^{-1}$ at 100° C. and 95% relative humidity.

Example 3c (This example illustrates the use of the organic solutions reported in the examples 1a-1b for preparing a hybrid membrane consisting of a polymeric matrix of a proton conducting ionomer of the state of art filled with an established percentage of the wished nano-particles. Case of Nafion filled with 10 wt % particles of composition $Zr(O_3P\text{—}OH)(O_3P\text{—}C_6H_4\text{—}SO_3H)$. The proton conductivities of membranes made of pure and hybrid ionomers are reported).

0.1 mol of anhydrous metasulfophenylenphosphonic acid and 0.1 mol of anhydrous phosphoric acid are dissolved in 200 g of propanol (solution a). Separately, 0.1 mol of anhydrous zirconium propionate (corresponding to 20.6 g) are dissolved in 200 g of propanol (solution b). The solution (a) is slowly added under stirring to solution (b) at room temperature thus obtaining a clear solution. Then, 0.51 g of this solution are added to 10 cm$^3$ of Nafion solution (37.5% 1-propanol, 37.5% 2-propanol, 20% water, 5% Nafion 1100). With this solution a membrane is prepared according to the procedure described in the previous example. A transparent membrane (thickness 0.015 cm) containing 10.0% wt/wt of $Zr(O_3P\text{—}OH)(O_3P\text{—}C_6H_4\text{—}SO_3H)$ is obtained. The proton conductivity is $7.2*10^{-2}$ S cm$^{-1}$ at 100° C. and 94% relative humidity.

As a summary it can be said that according to preferred embodiments the invention is based on the preparation of an organic solution of preferably phosphonic acids and tetravalent metals salts, preferably of Zr, Ti, Sn and Ce, in organic solvents, which behaves as a solution of layered tetravalent metals salts, preferably phosphate-phosphonates, which are completely insoluble in the known solvents. This peculiarity allows an easy insertion of particles of the above compounds in the pores of porous membranes, in the matrices of those polymers, which are soluble in the same organic solvents, as well as in the membrane/electrode interfaces of fuel cells. The use of tetravalent metals salts, preferably zirconium phosphate-phosphonates, possessing high proton conductivity (in some cases higher than $10^{-1}$ S cm$^{-1}$) allows the preparation of impregnated porous membranes and of nano-polymeric membranes combining good mechanical properties, and/or reduced permeability to gaseous species, with good proton conductivity.

These membranes can therefore be employed in fuel cells even at temperatures higher than 80° C. These membranes also possess a high catalytic activity and can therefore be employed in catalytic membrane reactors.

The invention claimed is:

1. Organic solutions containing metal(IV) salts and oxoacids of phosphorus from which, after evaporation of a solvent, insoluble compounds of general composition $M(IV)(O_3P\text{-}G)_{2-n}(O_3P\text{—}R^1\text{—}X)_n$ are obtained, where M(IV) is a tetravalent metal, -G is a generic inorganic or organic group, —R$^1$— is an organic group, —X is an acid group and n is a coefficient ranging from 0 to 1.5.

2. The organic solutions of claim 1 wherein the tetravalent metal salt is an anion and is selected from the group consisting of carboxylates, chlorides and alkoxides.

3. The organic solutions of claim 1 wherein the tetravalent metal salt is selected from the group consisting of Zr, Ti, Sn and Ce or their mixture.

4. The organic solutions of any of claims 1 wherein the tetravalent salt is zirconyl propionate or chloride.

5. The organic solutions of any of claim 1 wherein the group -G is selected from the group consisting of acid groups —OH; —R$^2$—SO$_3$H and —R$^2$—PO$_3$H$_2$; and where —R$^2$— is an organic group with linear chain selected from the group consisting of —(CH$_2$)$_m$— and —(CF$_2$)$_m$—.

6. The organic solutions of claim 1 wherein the group —R$^1$— is an arylene group selected from the group consisting of —C$_6$H$_4$—; —C$_6$H$_4$—CH$_2$— and —C$_6$H$_4$—CF$_2$—.

7. The organic solutions of claim 1 wherein the acid group —X selected from the group consisting of —SO$_3$H, —PO$_3$H$_2$ and —COOH.

8. The organic solutions of claim 1 wherein the organic solvent is a protonable solvent or solvents selected from the group consisting of N,N-dimethylformamide, N-methyl-2-pyrrolidone, dioxane, dimethylsulfoxide, acetamide, acetonitrile, various alkanols and mixtures thereof.

9. The process for the insertion of nano-particles of tetravalent metal salts within the pores of polymeric or inorganic porous membranes comprising:
   a) preparing the organic solution of claim 1; b) impregnating the porous membrane with the solution; c) eliminating the solvent; d) repeating the steps b) and c) until a partial or complete pore filling is obtained;
   wherein the tetravalent metal salts are phosphate-phosphonates; and
   wherein the organic solution prepared in step a) optionally comprises a polymer and/or an ionomer.

10. A method of preparing proton conducting composite membranes, comprising:
   a) preparing the organic solution of claim 1; b) impregnating a polymeric or inorganic porous membrane with the solution; c) eliminating the solvent; d) repeating steps b) and c) until a partial or complete pore filling is obtained;
   wherein the tetravalent metal salts are phosphate-phosphonates; and wherein the organic solution prepared in step a) optionally comprises a polymer and/or a proton conducting ionomer.

11. Proton conducting composite membranes, wherein the porous polymeric or inorganic membranes are impregnated with the organic solution of claim 1, and wherein the solvent has been eliminated.

12. The proton conducting composite membranes of claim 11 wherein the polymeric porous membrane is a polymer made of chemically and/or thermally stable polymers selected from the group consisting of, polytetrafluoroethylene (PTFE), polyvinylidene fluoride (PVDF), polyesters, polyethersulfones and fluoroelastomeres.

13. The proton conducting composite membranes of claim 11 wherein the pore dimensions of the porous membranes are in the range 0.02-20 μm and a porosity >10%.

14. The proton conducting composite membranes of claim 11 wherein the phosphate-phosphonates selected from the group consisting of $Zr(O_3P-CH_2-PO_3H_2)_2$ and compounds of the series $Zr(O_3P-OH)_{2-n}(O_3P-C_6H_4-SO_3H)_n$, and $Zr(O_3P-C_6H_4-SO_3H)_{2-n}(O_3P-CH_2-PO_3H_2)_n$, with n in the range 0.1-1.5.

15. A method of preparing conducting composite membranes, comprising:
   a) preparing the organic solution of claim 1; b) impregnation of a porous ceramic membrane with the solution; c) eliminating the solvent; d) repeating steps b) and c) until a partial pore filling is obtained;
   wherein the pores are partially filled with a tetravalent metal salt; and
   wherein the membranes exhibit catalytic activity.

16. The method of claim 15 wherein the tetravalent metal salts is a phosphate-phosphonate selected from the group consisting of $Zr(O_3P-CH_2-PO_3H_2)_2$ and compounds of the series $Zr(O_3P-OH)_{2-n}(O_3P-C_6H_4-SO_3H)_n$, and $Zr(O_3P-C_6H_4-SO_3H)_{2-n}(O_3P-CH_2-PO_3H_2)_n$, with n in the range 0.1-1.5.

17. A method for the preparation of nano-polymers constituted by nano-particles of tetravalent metal salts, comprising,
   a) preparing the organic solution of claim 1; and b) elimination of the solvent;
   wherein the tetravalent metal salts are phosphate-phosphonates; and
   wherein the organic solution prepared in step a) optionally comprises an organic or inorganic polymer or polymers thereby producing a matrix of organic or inorganic polymers soluble in the same solvents.

18. The method of claim 17 wherein the organic polymeric matrix is that of a proton conducting ionomer.

19. The method for preparing the nano-polymers and nano-ionomers of claim 18 wherein the elimination of the solvent is performed by evaporation or with a non-solvent of the polymer or ionomer.

20. Nano-polymers produced by the method of claim 17.

21. The nano-polymers of claim 20 wherein the matrix is a synthetic ionomer selected from the group consisting of perfluorosulphonic polymers, sulfonated polyetherketones (sPEK), sulfonated polyethersulfones and sulfonated polyvinylidenfluoride (sPVDF).

22. The nano-polymers of claim 20 wherein the nano-particles of tetravalent metal salts dispersed in the polymeric matrix exhibit proton conductivity $>10^{-2}$ S cm$^{-1}$ at 70° C. and 95% relative humidity.

23. The nano-polymers of claim 20 wherein the nano-particles of tetravalent metal salts are selected from the group consisting of $Zr(O_3P-CH_2-PO_3H_2)_2$ and compounds of the series $Zr(O_3P-OH)_{2-n}(O_3P-C_6H_4-SO_3H)_n$, and $Zr(O_3P-C_6H_4-SO_3H)_{2-n}(O_3P-CH_2-PO_3H_2)_n$, with n in the range 0.1-1.5.

24. A method for the preparation of membranes constituted by nano-polymers, comprising:
   a) preparing the organic solution of claim 1; and b) eliminating of the solvent;
   wherein the tetravalent metal salts are phosphate-phosphonates; and
   wherein the organic solution prepared in step a) optionally comprises an organic or inorganic polymer or polymers thereby producing a matrix of organic or inorganic polymers soluble in the same solvents.

25. The method of claim 24, wherein the membranes are nano-ionomeric proton conducting membranes.

26. A method for insertion of a large variety of lamellar nano-particles of tetravalent metal salts in the membrane/electrode interfaces of PEM FCs, comprising preparing the organic solutions according to claim 1 and eliminating the solvent.

27. A method according to claim 26, further comprising the addition of ionomers and/or other proton conducting compounds soluble in the same solvents.

28. An electrochemical device comprising the nano-polymers of claim 25.

29. The electrochemical device of claim 28, wherein said device is designed for generating electrical energy from the oxidation of a fuel.

30. A fuel cell for electrical vehicles and/or for portable electrical devices comprising the electrochemical device of claim 28.

31. Indirect methanol and direct methanol fuel cells comprising the electrochemical device of claim 28.

32. A catalytic membrane reactors comprising the proton conducting composite membranes produced according to claim 10.

* * * * *